(12) United States Patent  (10) Patent No.: US 11,043,301 B2
Hung et al.  (45) Date of Patent: *Jun. 22, 2021

(54) INFRARED DETECTORS AND THERMAL TAGS FOR REAL-TIME ACTIVITY MONITORING

(71) Applicant: INTERNATIONAL BUSINESS MACHINES CORPORATION, Armonk, NY (US)

(72) Inventors: Li-Wen Hung, Mahopac, NY (US); Jui-Hsin Lai, White Plains, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/661,255

(22) Filed: Oct. 23, 2019

(65) Prior Publication Data

US 2020/0058394 A1 Feb. 20, 2020

Related U.S. Application Data

(63) Continuation of application No. 15/205,666, filed on Jul. 8, 2016, now Pat. No. 10,522,251.

(51) Int. Cl.
*G16H 40/63* (2018.01)
*G01J 5/00* (2006.01)
(Continued)

(52) U.S. Cl.
CPC .......... *G16H 40/63* (2018.01); *G01J 5/0025* (2013.01); *G01J 5/025* (2013.01); *G01J 5/089* (2013.01);
(Continued)

(58) Field of Classification Search
None
See application file for complete search history.

(56) References Cited

U.S. PATENT DOCUMENTS 4,051,726 A * 10/1977 Hastbacka .......... G01F 23/2927
250/577
4,490,053 A 12/1984 Coston et al.
(Continued)

FOREIGN PATENT DOCUMENTS

CN 201100973 Y 8/2008
CN 101651784 A 2/2010
(Continued)

OTHER PUBLICATIONS

Zhou, Z. et al., "A Real-time System for In-home Activity Monitoring of Elders" 31st Annual International Conference of the IEEE EMBS (Sep. 2009) pp. 6115-6118.
(Continued)

*Primary Examiner* — Nancy Bitar
(74) *Attorney, Agent, or Firm* — Tutunjian & Bitetto, P.C.; Kristofer Haggerty

(57) ABSTRACT

Methods and systems for activity monitoring include capturing an infrared image of an environment that comprises at least one patient being monitored and at least one infrared-emitting tag. A relationship between the patient being monitored and the at least one infrared-emitting tag is determined. An activity conducted by the patient being monitored is determined based on the relationship between the patient being monitored and the at least one infrared-emitting tag. A course of treatment for the patient being monitored is adjusted based on the determined activity.

19 Claims, 4 Drawing Sheets

(51) Int. Cl.
    *G06K 9/00*           (2006.01)
    *G06K 9/20*           (2006.01)
    *G16H 20/30*         (2018.01)
    *G01J 5/02*           (2006.01)
    *G01J 5/08*           (2006.01)

(52) U.S. Cl.
    CPC ....... *G06K 9/00771* (2013.01); *G06K 9/2018* (2013.01); *G16H 20/30* (2018.01); *G01J 2005/0077* (2013.01)

(56) References Cited

U.S. PATENT DOCUMENTS

| | | |
|---|---|---|
| 4,602,159 A | 7/1986 | Kasahara et al. |
| 4,733,079 A | 3/1988 | Adams et al. |
| 4,998,010 A | 3/1991 | Chandler et al. |
| 5,054,936 A | 10/1991 | Fraden |
| 5,357,095 A | 10/1994 | Weyrauch et al. |
| 5,414,405 A | 5/1995 | Hogg et al. |
| 5,585,625 A | 12/1996 | Spies |
| 5,678,928 A | 10/1997 | Agari |
| 5,689,241 A | 11/1997 | Clarke, Sr. et al. |
| 5,736,723 A | 4/1998 | Clarke et al. |
| 5,817,012 A | 10/1998 | Schoendorfer |
| 6,104,295 A | 8/2000 | Gaisser et al. |
| 6,297,511 B1 | 10/2001 | Syllaios et al. |
| 7,152,805 B2 | 12/2006 | Walmsley et al. |
| 7,290,720 B2 | 11/2007 | Walmsley et al. |
| 7,397,380 B1* | 7/2008 | Smolsky ............... A61B 5/015 340/573.1 |
| 8,256,113 B2 | 9/2012 | Hochstein |
| 8,637,897 B2 | 1/2014 | Kim et al. |
| 8,657,758 B2 | 2/2014 | Lia et al. |
| 8,659,423 B2 | 2/2014 | Kuris et al. |
| 8,692,221 B2 | 4/2014 | Ford |
| 9,060,714 B2 | 6/2015 | Bajcsy et al. |
| 9,176,990 B2 | 11/2015 | Stuart et al. |
| 9,291,607 B2 | 3/2016 | Chen et al. |
| 9,765,934 B2 | 9/2017 | Rogers et al. |
| 9,823,747 B2 | 11/2017 | Underkoffler et al. |
| 2004/0119603 A1 | 6/2004 | Bohlander et al. |
| 2007/0291473 A1* | 12/2007 | Traynor ................ A01K 11/00 362/106 |
| 2008/0138289 A1 | 6/2008 | Goronkin et al. |
| 2010/0011982 A1 | 1/2010 | Wich |
| 2010/0086235 A1 | 4/2010 | Loughrey et al. |
| 2010/0182153 A1 | 7/2010 | Jensen |
| 2010/0189313 A1 | 7/2010 | Prokoski |
| 2011/0001605 A1* | 1/2011 | Kiani ................... G06F 19/3418 340/5.6 |
| 2011/0025603 A1 | 2/2011 | Underkoffler et al. |
| 2011/0105854 A1* | 5/2011 | Kiani ..................... G16H 40/63 600/300 |
| 2011/0163683 A1* | 7/2011 | Steele ..................... F21V 23/02 315/192 |
| 2012/0191164 A1 | 7/2012 | Gander et al. |
| 2012/0215113 A1 | 8/2012 | Yarden et al. |
| 2012/0320216 A1 | 12/2012 | Mkrtchyan et al. |
| 2013/0079605 A1 | 3/2013 | Bandaru et al. |
| 2014/0148733 A1 | 5/2014 | Stone et al. |
| 2014/0276167 A1 | 9/2014 | Dasupta et al. |
| 2014/0332667 A1 | 11/2014 | Aramaki et al. |
| 2014/0341588 A1 | 11/2014 | Pederson |
| 2015/0002023 A1 | 1/2015 | Imangholi et al. |
| 2015/0123788 A1 | 5/2015 | Greenberg et al. |
| 2016/0065909 A1* | 3/2016 | Derenne et al. .... G01F 23/2927 250/577 |
| 2017/0332904 A1 | 11/2017 | Gannon et al. |
| 2018/0011982 A1 | 1/2018 | Hung et al. |
| 2018/0028072 A1 | 2/2018 | Shi |
| 2019/0206671 A1 | 7/2019 | Zissing et al. |

FOREIGN PATENT DOCUMENTS

| | | |
|---|---|---|
| CN | 101957929 A | 1/2011 |
| CN | 102483877 A | 5/2012 |
| CN | 102435142 A | 7/2013 |
| CN | 103617997 A | 3/2014 |
| CN | 103013520 B | 6/2014 |
| CN | 105308657 A | 2/2016 |
| CN | 105590901 A | 5/2016 |
| CN | 205197971 U | 5/2016 |
| CN | 105675155 A | 6/2016 |
| CN | 205909828 U | 1/2017 |
| DE | 202012011209 | 8/2013 |
| EP | 0813073 A2 | 12/1997 |
| FR | 2595852 A1 | 9/1987 |
| FR | 2932302 A1 | 12/2009 |
| JP | H0815007 A | 1/1996 |
| JP | 8295322 | 11/1996 |
| JP | 2001038979 A | 2/2001 |
| JP | 2006231296 A | 9/2006 |
| JP | 2006268607 A | 10/2006 |
| JP | 2007-127536 A | 5/2007 |
| JP | 2007127536 A | 5/2007 |
| JP | 2007199993 A | 8/2007 |
| JP | 4491285 62 | 6/2010 |
| JP | 2011192236 A | 9/2011 |
| JP | 4798808 B1 | 10/2011 |
| JP | 2012528405 A | 11/2012 |
| JP | 2012256575 A | 12/2012 |
| JP | 201490424 A | 5/2014 |
| JP | 2014104586 A | 6/2014 |
| KR | 20060089335 A | 8/2006 |
| TW | M265283 U | 5/2005 |
| WO | 9318476 A1 | 9/1993 |
| WO | 00/6551 | 11/2000 |
| WO | 2010138743 A2 | 12/2010 |
| WO | 2016011788 A1 | 1/2016 |

OTHER PUBLICATIONS

Jalal, A. et al., "A depth video sensor-based life-logging human activity recognition system for elderly care in smart indoor environments" Sensors (Jul. 2014) pp. 11735-11759, vol. 14, No. 7.
Office Action dated Apr. 5, 2018 for U.S. Appl. No. 15/296,090.
Perez-Cabre, et al., "Near Infrared Multifactor Identification Tags," Optics Express, Nov. 2007, 13 pages, vol. 15, No. 23.
Wikipedia, "QR Code," www.wikipedia.org, Modified Oct. 2016, pp. 1-16, available at: https://en.wikipdia.org/wiki/QR_code.
Zang, "Covert IR Optical Taggants Enhance Identification," Photonics Spectra, Feb. 2014, 8 pages.
Versus, "Versus Announces New Wi-Fi Real-time Locating Platform and Asset Tag," www.VerusTech.com, Dec. 2015, 2 pages, available at http://www.versustech.com/rtls-news/press-releases/new-wi-fi-rtls-asset-tag/.
U.S. Office Action issued in U.S. Appl. No. 15/296,115, dated Sep. 24, 2018, pp. 1-20.
U.S. Final Office Action issued in U.S. Appl. No. 15/296,115, dated Dec. 26, 2018, pp. 1-10.
International Search Report Issued in PCT/IB2017/056225 dated Jan. 25, 2018, 11 pages.
Notice of Allowance for U.S. Appl. No. 15/296,115 dated Apr. 3, 2019, 11 pages.
Non Final Rejection for U.S. Appl. No. 16/425,417 dated Aug. 15, 2019 (28 pages).
U.S. Office Action issued in U.S. Appl. No. 16/425,417, dated Mar. 9, 2020, pp. 1-10.
U.S. Notice of Allowance issued in U.S. Appl. No. 16/425,417 dated Jul. 1, 2020, pp. 1-12.
U.S. Notice of Allowance issued in U.S. Appl. No. 16/425,417, dated Aug. 20, 2020, 21 pages.
International Search Report for PCT/IB2017/055592, dated Dec. 28, 2017, 12 pages.
U.S. Notice of Allowance issued in U.S. Appl. No. 16/425,417 dated Jul. 1, 2020, 12 pages.

(56) References Cited

OTHER PUBLICATIONS

Chinese Office Action for 201780064193.9 dated Jul. 30, 2020, 10 pages.
JP Notice of Allowance issued in Japanese Patent Application No. 2019-518246 dated Jan. 20, 2021, pp. 1-5.
List of IBM Patents or Patent Applications Treated as Related dated Oct. 23, 2019, 2 pages.
Japanese Notice of Allowance issued in Japanese Patent Application No. 2019-518065, dated Mar. 12, 2021, pp. 1-2.

* cited by examiner

INFRARED DETECTORS AND THERMAL TAGS FOR REAL-TIME ACTIVITY MONITORING

BACKGROUND

Technical Field

The present invention generally relates to activity monitoring and, in particular, to the use of infrared imaging and thermal tags to track activity with minimal privacy concerns.

Description of the Related Art

There is a significant need to monitor patient activity, for example during convalescence or for elder care in the home. In such cases, a doctor may need to know how treatments, or the symptoms of a disease, are progressing despite the patient being at a remote location.

However, conventional video monitoring poses significant privacy concerns. In particular, while a conventional color camera provides the ability to remotely monitor a patient's activity, such cameras will also capture information that may include, for example, images displayed on a computer or television screen or the writing on a sheet of paper. As a result, patients may be reluctant to allow such monitoring, despite the definite benefits that the monitoring might otherwise provide.

SUMMARY

A method for activity monitoring includes capturing an infrared image of an environment that comprises at least one patient being monitored and at least one infrared-emitting tag. A relationship between the patient being monitored and the at least one infrared-emitting tag is determined using a processor. An activity conducted by the patient being monitored is determined based on the relationship between the patient being monitored and the at least one infrared-emitting tag. A course of treatment for the patient being monitored is adjusted based on the determined activity.

A method for activity monitoring includes capturing infrared video of an environment from multiple angles. The environment includes at least one patient being monitored and at least one infrared-emitting tag that is attached to and identifies a particular object in the environment. A relationship between the patient being monitored and the at least one infrared-emitting tag is determined using a processor. The relationship is tracked between the multiple angles and across multiple frames of each infrared video. An activity conducted by the patient being monitored is tracked based on the relationship between the patient being monitored and the at least one infrared-emitting tag. A course of treatment for the patient being monitored is adjusted based on the determined activity.

A system for activity monitoring includes at least one infrared-emitting tag. An infrared monitoring device is configured to capture an infrared image of an environment that comprises at least one human being and the at least one infrared-emitting tag. An image analysis module includes a processor and a memory and is configured to determine a relationship between the human being and the at least one infrared-emitting tag. An activity module is configured to determine an activity conducted by the human being based on the relationship between the human being and the at least one infrared-emitting tag. An alert module is configured to adjust a course of treatment for the patient being monitored based on the determined activity.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Embodiments of the present invention use infrared cameras for activity monitoring. Infrared imaging detects electromagnetic radiation in the infrared band, which is invisible to the naked eye and which is commonly created by warm objects (such as, e.g., the human body). Infrared light can also be generated by artificial means. As such, the present embodiments track motion of the patient using the infrared camera and, in addition, tracks the patient's interactions with objects in the environment through the use of infrared emitting tags attached to objects of interest.

Figure 1:
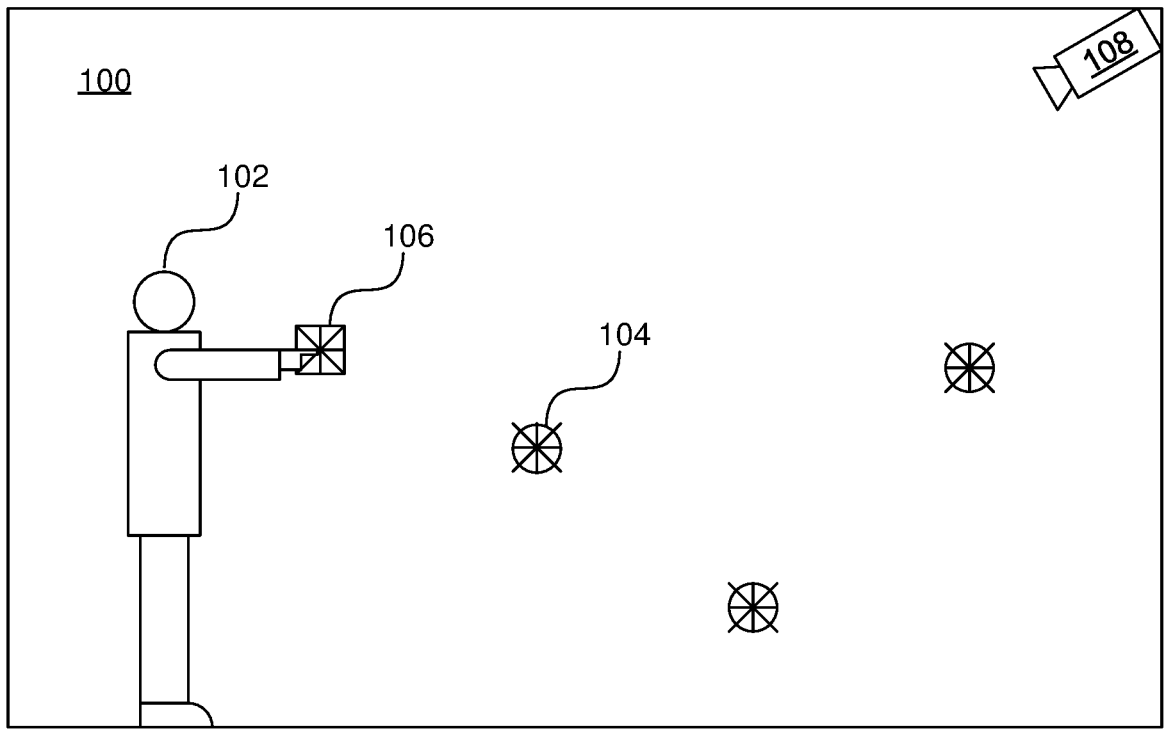
FIG. 1 is a diagram of a monitored environment in accordance with the present principles.

Referring now to FIG. 1, an exemplary monitoring environment 100 is shown. The environment 100 includes one user 102. The user 102 may be, for example, a person who is injured or sick, an elderly person, or any person who would benefit from activity monitoring. In addition, a number of objects 104 are present in the environment 100 that include thermal tags. The objects 104 emit a continuous or pulsed infrared signal via the thermal tags. In an embodiment using a pulsed infrared signal, each object 104 may be assigned a unique pattern that distinguishes the object from other objects.

An infrared monitoring device 108 captures infrared information from the environment. It should be noted that multiple monitoring devices 108 may be used in a single environment to cover all of the potential angles of view. The monitoring device 108 may take still images or may alternatively capture video of the infrared emissions of the environment 100. It should be understood that the present principles may be applied to other types of imaging device, but infrared is particularly contemplated because human bodies inherently emit detectable levels of infrared radiation. Limiting the monitoring device 108 strictly to infrared is not needed for the functioning of the present embodiments, but serves to prevent potential privacy infringement that might arise from recording visible light information.

The user 102 emits infrared radiation by virtue of body heat, while the objects 104 emit infrared radiation from their respective thermal tags. This infrared light is captured by the monitoring device 108 and can be used to show the user's activities in the environment 100. For example, if the user 102 picks up an object 106 (e.g., a cane), the monitoring device 108 will capture that event. However, being limited to infrared radiation, the monitoring device 108 will not detect untagged objects unless they differ in temperature from the ambient temperature. As a result, the monitoring device 108 is not able to resolve the details of printed subject matter or the display of screens, as these surfaces generally present a uniform temperature that does not depend on the content.

The information captured by the monitoring device 108 can be of significant use in medical treatment. It may be of interest, for example, how often a patient suffering from Parkinson's disease uses a cane. A thermal tag may therefore be attached to the cane, such that instances where the user 102 is carrying the cane may be recorded and logged.

Figure 2:
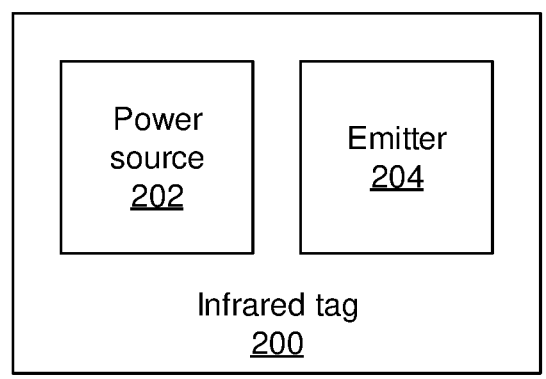
FIG. 2 is a block diagram of an infrared-emitting tag in accordance with the present principles.

Referring now to FIG. 2, a diagram of an exemplary infrared tag 200 is shown. The tag 200 includes a power source 202 and an emitter 204. The power source 202 may be any appropriate device for storing or generating electrical power. In one example, the power source 202 may be a simple battery (e.g., a coin cell or other small battery). In another example, the power source 202 may convert power from, e.g., light or motion into electrical energy that may then be stored in a battery or capacitor.

The power source 202 supplies electrical power to the emitter 204. In one embodiment, the emitter 204 may be a set of resistive paths laid out in a pattern. When a current is passed through the resistive paths, heat is generated and infrared light is emitted. The layout of these resistive paths may be made unique to each infrared tag 200, such that a monitoring device 108 can recognize the pattern and thereby identify the object 104 to which the infrared tag 200 is attached.

In an alternative embodiment, the emitter 204 may include an infrared light emitting diode (LED) that emits an infrared signal when a current passes through it. As above, a unique pattern of infrared LEDs may be laid out for each infrared tag 200. Alternatively, the output of the infrared LED may be modulated according to a unique pattern.

The infrared tags 200 may be attached with a known orientation and location on each object 104 of interest in the environment 100. Based on the images captured by the monitoring device 108, which show only the contour of the user's body 102 the infrared pattern being emitted by the tags 200, images of the user's walking patterns and interactions with the objects 104 can be reconstructed.

Figure 3:
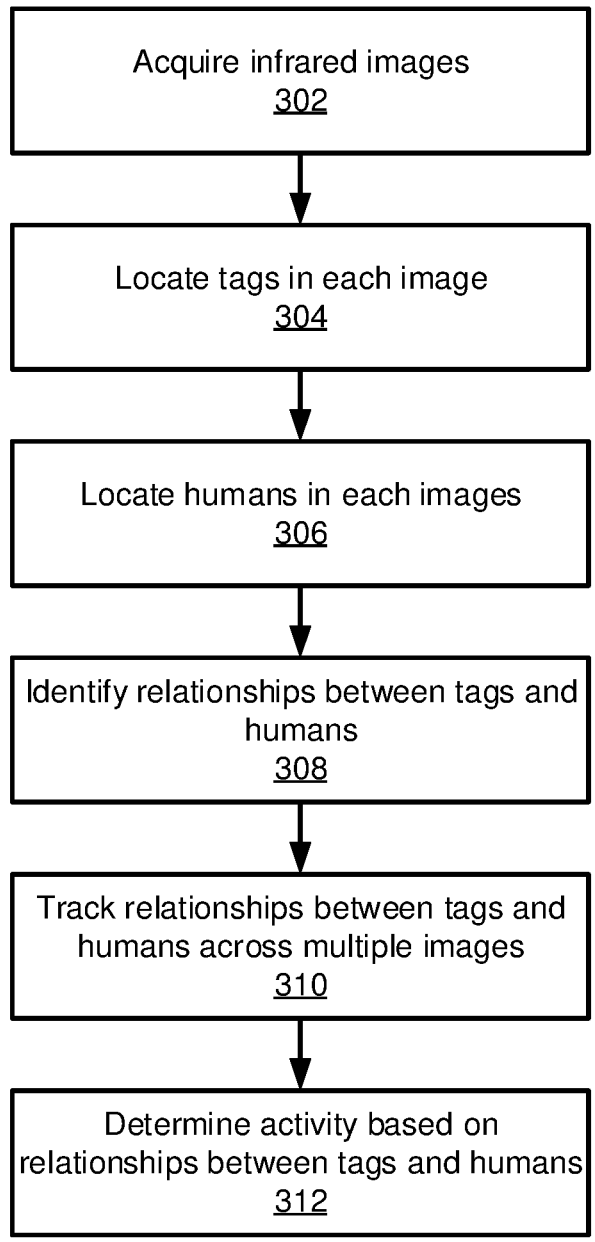
FIG. 3 is a block/flow diagram of a method for determining activities of a monitored person in accordance with the present principles.

Referring now to FIG. 3, a method of monitoring activity is shown. Block 302 acquires infrared images of the environment 100 using the monitoring device 108. While other forms of imaging are possible, it should be understood that using only infrared images provides the ability to easily track a user's activity while also preserving as much of the user's privacy as possible.

Block 304 locates any infrared tags 200 that might be present in each image. As noted above, the tags 200 may be attached to objects 104 in the environment, and such objects may be fixed or movable. The tags 200 can be located by searching in an image for relatively bright, relatively small patterns in the infrared image. The patterns will be unique to the individual tag 200, either in spatial layout or in temporal sequence. As such, block 304 can identify the object 104 to which the tag 200 is attached.

Block 306 locates humans in each image. Humans put out a characteristic pattern of infrared radiation, which will appear as a silhouette in the infrared images. Because the monitoring device 108 responds to light put out according to the warmth of the body, it cannot distinguish fine details such as, e.g., lip movements, which can be privacy sensitive.

Block 308 identifies relationships between the tags 200 located in block 304 and humans detected in block 306. For example, if tag 200 overlaps with a human's silhouette in the infrared image, the human may be interacting with that tag 200. In one specific example, block 308 attempts to correlate the location of the tag 200 with that of the human in each of the images. If the location of the tag 200 correlates with that of the human in each detected image, then block 308 determines that the human is interacting with the tag. If, however, the tag 200 only overlaps with the human's silhouette in one of three images, then in this example it can be concluded that the person is not actually nearby the tag 200.

It should be noted that the tag 200 may not overlap with a person's silhouette during an interaction. For example, a tag 200 may be attached on one end of a cane, while the person holds the other end of the cane. However, relationships can still be deduced from patterns of relative motion over time in video.

It should be understood that the monitoring device 108 may be sensitive to a range of different infrared wavelengths. In particular, human beings put out infrared emissions at relatively long wavelengths (e.g., greater than about 1 μm). The tags 200 may therefore be configured to emit infrared radiation at relatively short wavelengths (e.g., less than about 1 μm). This allows the system to readily distinguish between humans and tags 200, even when the tag visually overlaps with the human's silhouette.

Block 310 tracks the identified relationships across multiple images. Block 312 then uses the relationships between people and tagged objects, in both space and time, to determine activities. For example, if the human silhouette and a given tag 200 move across the field of view of the monitoring device 108, it can be deduced that the person is holding the object 104 that the tag 200 is attached to. In this example, block 312 therefore tracks the spatial relationship between the person and the tag 200 across multiple frames of a recorded video from the monitoring device 108.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 4:
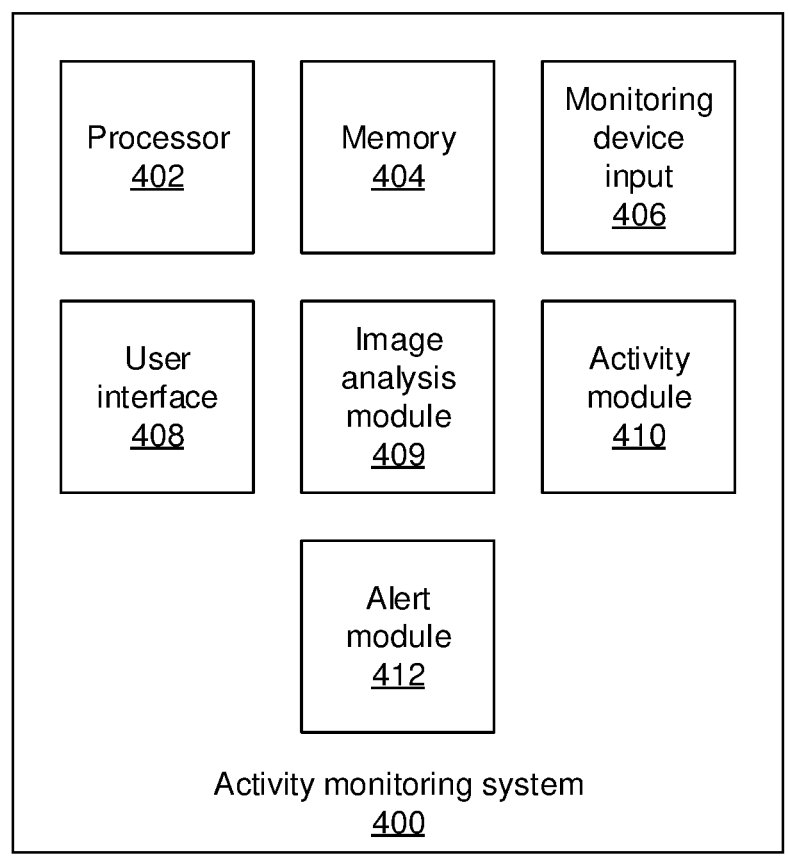
FIG. 4 is a block diagram of an activity monitoring system in accordance with the present principles.

Referring now to FIG. 4, an activity monitoring system 400 is shown. The system 400 includes a hardware processor 402 and memory 404. In addition, the system 400 receives image information from the one or more monitoring devices 108 via monitoring device input 406. A user interface 408 allows an operator to monitor current and stored activity information without infringing on the monitored person's privacy any more than is necessary.

In addition, the activity monitoring system includes functional modules that may be implemented as software that is stored in memory 404 and executed by processor 402. In an alternative embodiment, the functional modules may be implemented as one or more discrete hardware components, for example in the form of field programmable gate arrays or application specific integrated chips. An analysis module 409 analyzes the images received by the monitoring device input 406 and locates human shapes and tags 200 in each image. An activity module 410 then correlates the positions of human shapes and tags 200 in both time and space and determines relationships between them. Based on the determined relationships, conclusions can be automatically drawn regarding a person's activities.

An alert module 412 is included to provide an alert to an operator if the activity module determines that one or more conditions is satisfied. The alert module 412 may alternatively provide any of a variety of functions. In a first example, the alert module 412 may remind a patient to adhere to a routine. In this first example, the system can detect whether a user has interacted with a tagged pill bottle (based on the detected interaction with the tagged bottle) and taken medication (based on the user's detected motions). If a routine of taking the medication at a specific time is broken, the alert module 412 can communicate with the patient or caretaker to provide a reminder.

In a second example, for a patient with a chronic disease, treatment may depend on the seriousness and frequency of symptoms, such as imbalance, gait change, or slowness of motion. Some symptoms occur sporadically, and it can be difficult to obtain a complete picture of a patient's symptoms when the doctor relies on only the patient's feelings and memories to judge the severity and frequency of symptoms. The alert module 412 can therefore keep a log of events, their frequency, their severity, and any surrounding conditions as they occur for later review.

The alert module 412 may furthermore provide an alert if life-threatening or abnormal behavior or events occur. For example, if the system detects that the person has fallen down and has been on the floor for an extended period of time, the alert module 412 can provide this information to caretakers.

Figure 5:
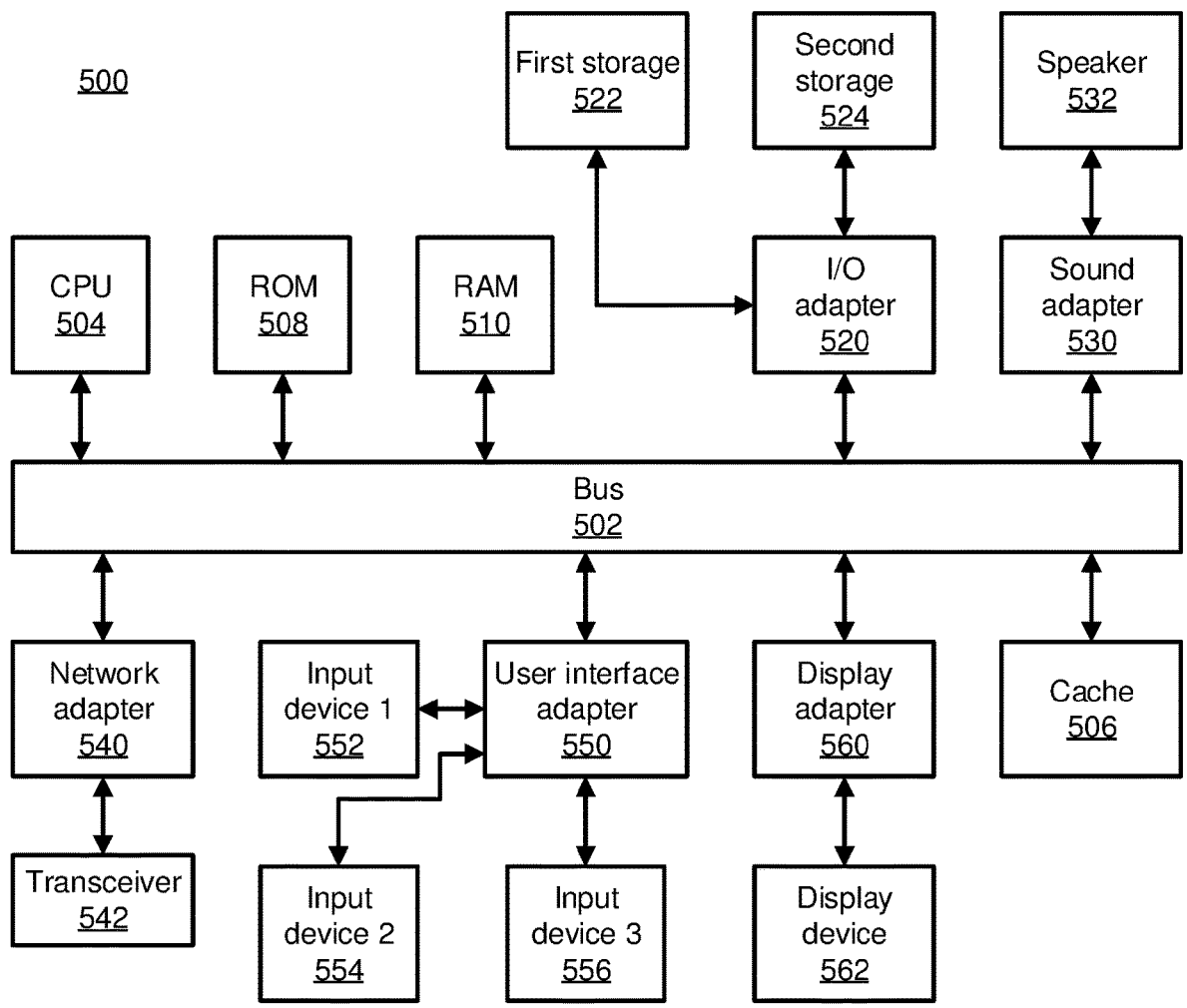
FIG. 5 is a block diagram of a processing system in accordance with the present principles.

Referring now to FIG. 5, an exemplary processing system 500 is shown which may represent the activity monitoring system 400. The processing system 500 includes at least one processor (CPU) 504 operatively coupled to other components via a system bus 502. A cache 506, a Read Only Memory (ROM) 508, a Random Access Memory (RAM) 510, an input/output (I/O) adapter 520, a sound adapter 530, a network adapter 540, a user interface adapter 550, and a display adapter 560, are operatively coupled to the system bus 502.

A first storage device 522 and a second storage device 524 are operatively coupled to system bus 502 by the I/O adapter 520. The storage devices 522 and 524 can be any of a disk storage device (e.g., a magnetic or optical disk storage device), a solid state magnetic device, and so forth. The storage devices 522 and 524 can be the same type of storage device or different types of storage devices.

A speaker 532 is operatively coupled to system bus 502 by the sound adapter 530. A transceiver 542 is operatively coupled to system bus 502 by network adapter 540. A display device 562 is operatively coupled to system bus 502 by display adapter 560.

A first user input device 552, a second user input device 554, and a third user input device 556 are operatively coupled to system bus 502 by user interface adapter 550. The user input devices 552, 554, and 556 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 552, 554, and 556 can be the same type of user input device or different types of user input devices. The user input devices 552, 554, and 556 are used to input and output information to and from system 500.

Of course, the processing system 500 may also include other elements (not shown), as readily contemplated by one of skill in the art, as well as omit certain elements. For example, various other input devices and/or output devices can be included in processing system 500, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 500 are readily contemplated by one of ordinary skill in the art given the teachings of the present principles provided herein.

Having described preferred embodiments of infrared detectors and thermal tags for real-time activity monitoring (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for activity monitoring, comprising:
    capturing an infrared image of an environment that comprises at least one person being monitored and at least one infrared-emitting tag, each infrared-emitting tag including a plurality of resistive paths that are laid out in a unique spatial pattern and that generate heat and infrared light when a current runs through them;
    emitting an infrared pattern from the at least one infrared-emitting tag;
    determining an activity relationship between the person being monitored and the at least one infrared-emitting tag, based on the emitted infrared pattern, using a processor; and
    adjusting a course of treatment for the person being monitored based on the determined activity relationship.

2. The method of claim 1, wherein each infrared-emitting tag comprises a unique spatial layout that emits infrared radiation in a unique spatial pattern.

3. The method of claim 1, wherein a wavelength of infrared radiation emitted by the infrared-emitting tag is shorter than wavelengths of infrared radiation generally emitted by a human body.

4. The method of claim 1, wherein capturing the infrared image comprises capturing infrared video of the environment and wherein determining the activity relationship between the person and the at least one infrared-emitting tag comprises tracking a spatial relationship between the person and the at least one infrared-emitting tag across consecutive frames of the infrared video.

5. The method of claim 1, wherein each infrared-emitting tag is attached to, and identifies, a particular object in the environment.

6. The method of claim 1, wherein capturing the infrared image comprises capturing multiple images from multiple monitoring devices to obtain views of the environment from multiple angles.

7. The method of claim 6, wherein determining the activity relationship between the person being monitored and the at least one infrared-emitting tag comprises locating each infrared-emitting tag in at least one infrared image and determining whether a boundary of each object represented by each infrared-emitting tag overlaps a silhouette of the person being monitored in each image that includes the respective infrared-emitting tag.

8. The method of claim 6, wherein determining the activity relationship comprises determining that the person being monitored is interacting with an object to which an infrared-emitting tag is attached if a boundary of each object represented by an infrared-emitting tag overlaps the silhouette of the person being monitored in each image that includes the respective infrared-emitting tag.

9. A non-transitory computer readable storage medium comprising a computer readable program for activity monitoring, wherein the computer readable program when executed on a computer causes the computer to perform the steps of:
   capturing an infrared image of an environment that comprises at least one person being monitored and at least one infrared-emitting tag, each infrared-emitting tag including a plurality of resistive paths that are laid out in a unique spatial pattern and that generate heat and infrared light when a current runs through them;
   emitting an infrared pattern from the at least one infrared-emitting tag;
   determining an activity relationship between the person being monitored and the at least one infrared-emitting tag, based on the emitted infrared pattern, using a processor; and
   adjusting a course of treatment for the person being monitored based on the determined activity relationship.

10. A system for activity monitoring, comprising:
   at least one infrared-emitting tag that emits an infrared pattern and that includes a plurality of resistive paths that are laid out in a unique spatial pattern and that generate heat and infrared light when a current runs through them;
   an infrared camera configured to capture an infrared image of an environment that comprises at least one person being monitored and the at least one infrared-emitting tag;
   a hardware processor; and
   a memory that stores computer program code which, when executed by the hardware processor, implements:
      image analysis code that determines an activity relationship between the person being monitored and the at least one infrared-emitting tag, based on the emitted infrared pattern; and
      alert code that adjusts a course of treatment for the person being monitored based on the determined activity relationship.

11. The system of claim 10, wherein each infrared-emitting tag comprises a unique spatial layout that emits infrared radiation in a unique spatial pattern.

12. The system of claim 10, wherein a wavelength of infrared radiation emitted by the infrared-emitting tag is shorter than wavelengths of infrared radiation generally emitted by a human body.

13. The system of claim 10, wherein the infrared camera is further configured to capture infrared video of the environment.

14. The system of claim 13, wherein the image analysis code further tracks a spatial relationship between the person and the at least one infrared-emitting tag across consecutive frames of the infrared video.

15. The system of claim 10, wherein each infrared-emitting tag is attached to, and identifies, a particular object in the environment.

16. The system of claim 10, further comprising a plurality of infrared monitoring devices, positioned to capture respective infrared images to obtain views of the environment from multiple angles.

17. The system of claim 10, wherein the image analysis code further locates each infrared-emitting tag in at least one infrared image and determines whether a boundary of each object represented by each infrared-emitting tag overlaps a silhouette of the person being monitored in each image that includes the respective infrared-emitting tag.

18. The system of claim 17, wherein the image analysis code further determines that the person being monitored is interacting with an object to which an infrared-emitting tag is attached if a boundary of each object represented by an infrared-emitting tag overlaps the silhouette of the person being monitored in each image that includes the respective infrared-emitting tag.

19. The method of claim 1, wherein the activity relationship includes a distance between the person being monitored and the at least one infrared-emitting tag.

* * * * *